United States Patent [19]

Jones et al.

[11] Patent Number: 4,937,209
[45] Date of Patent: * Jun. 26, 1990

[54] POROUS INORGANIC MATERIALS

[75] Inventors: Thomas R. Jones; Caryl Gould, both of St. Austell, United Kingdom; Alan J. Brown, Tennille, Ga.; Roger James, St. Austell, United Kingdom

[73] Assignee: ECC International Limited, England

[ * ] Notice: The portion of the term of this patent subsequent to May 2, 2006 has been disclaimed.

[21] Appl. No.: 248,437

[22] Filed: Sep. 23, 1988

Related U.S. Application Data

[63] Continuation-in-part of Ser. No. 22,944, Mar. 6, 1987, Pat. No. 4,826,789, which is a continuation-in-part of Ser. No. 698,323, Feb. 5, 1985, abandoned.

[30] Foreign Application Priority Data

Feb. 9, 1984 [GB]  United Kingdom ................. 8403395
Sep. 24, 1987 [GB] United Kingdom ................. 8722451

[51] Int. Cl.$^5$ ...................... C04B 38/04; C12N 11/14; C12N 5/00
[52] U.S. Cl. ....................................... 501/80; 435/176; 435/240.23; 501/68; 523/218; 523/219
[58] Field of Search ........................... 501/5, 6, 68, 80; 435/176, 240.23; 523/218, 219

[56] References Cited

U.S. PATENT DOCUMENTS

| 2,556,122 | 1/1951 | Bertorelli et al. | 423/131 |
| 2,939,764 | 6/1960 | Schoenfelder et al. | 423/131 |
| 4,389,385 | 6/1983 | Ramsay | 423/328 |
| 4,826,789 | 5/1989 | Jones et al. | 502/68 |

FOREIGN PATENT DOCUMENTS

| 22146 | 5/1972 | Australia . |
| 0130734 | 1/1985 | European Pat. Off. . |
| 0155669 | 9/1985 | Fed. Rep. of Germany . |
| 1213093 | 11/1970 | United Kingdom . |
| 1457890 | 12/1976 | United Kingdom . |

*Primary Examiner*—Allan M. Lieberman
*Attorney, Agent, or Firm*—Klauber & Jackson

[57] ABSTRACT

There is provided a porous cellular material comprising a plurality of cavities each defined by a substantially spherical wall formed of a rigid intermeshing matrix of ceramic needles said wall being pierced by at least one aperture to provide access to the cavity, and the or each aperture having a diameter such that the ratio of the diameter of the aperture to the diameter of the cavity into which the aperture opens is in the range of from 0.1:1 to 1:1.

12 Claims, 11 Drawing Sheets

|← 5.5μm

|← 0.5μm

→| |← 5μm

→| |← 0.5μm

← 0.5μm →

← 55μm →

5 μm

5 μm 0.5μm

5μm

5μm

5μm

THE GROWTH OF SACCHAROMYCES CEREVISIAE
ON A 7g PACKED BED OF BIOFIX D12

POROUS INORGANIC MATERIALS

This is a continuation-in-part of application Ser. No. 022,944, filed Mar. 6, 1987, now U.S. Pat. No. 4,826,789, which is a continuation-in-part of application Ser. No. 698,323, filed Feb. 5, 1985, now abandoned.

BACKGROUND OF THE INVENTION

This invention relates to a porous cellular material for supporting and immobilising biological catalysts, especially but not exclusively whole living cells.

DESCRIPTION OF THE PRIOR ART

Hitherto, two principal methods have been used for immobilising biological catalysts, namely: (i) adsorption of the catalyst to, and (ii) entrapment of the catalyst within, a water-insoluble immobilisation matrix.

Adsorption of the catalyst to the outer surface of a matrix is rarely satisfactory because the intermolecular forces holding the catalyst to the support are generally insufficient to prevent sloughing or flushing away of the catalyst by a flowing liquid stream.

Entrapment of the catalyst within a matrix most frequently makes use of a matrix of calcium alginate. A suspension of the catalyst to be immobilised is mixed with a solution of sodium alginate, and calcium ions are added to the mixture to form a calcium alginate gel in which the catalyst particles are entrapped. Advantageously the gel is prepared in the form of discrete beads. This method suffers from the disadvantages that it is difficult to carry out on a commercial scale and that it is necessary for the catalyst particles to be separated from the medium in which they were grown and to be concentrated before they can be incorporated in the beads of gel. Also the permeability of the gel to liquids is relatively low so that, for example, biological cells trapped near the centre of calcium alginate beads would be reached only with difficulty by nutrient solution diffusing in from the bead surface. Further disadvantages of the use of calcium alginate are that the beads have poor mechanical strength and are therefore unsuitable for use on a large commercial scale and that, in the presence of certain chelating agents, in particular water-soluble phosphate salts which are often used for preparing buffer solutions for biochemical reactions, calcium ions are extracted from the calcium alginate gel causing the beads to collapse.

Ideally, an immobilisation matrix for relatively large biological catalyst particles such as whole living cells should have a structure which is sufficiently rigid to provide a relatively distortion-free cavity for each catalyst particle, even under the forces which occur in the packed columns used for large scale treatment processes, while being sufficiently porous to permit easy access of the catalyst particles into the cavities and to allow free circulation of nutrient liquids.

An organic polymer which has a molecular structure in the form of a three dimensional network and which is reversibly permeable to nutrient solutions but not to biological cells is a theoretical possibility, but in practice most cross-linking reagents which are known to be capable of creating a polymer of the type required have a toxic or inhibitory effect on living cells. Also, no polymer is yet known which has sufficient rigidity to remain undistorted in a large scale packed column. In order to avoid the problem of the toxicity of the cross-linking reagents it might be possible to introduce cells into a ready formed polymer network but at present there appears to be no practical technique available for doing this.

Mullite is an aluminosilicate material which exists in the form of needle-shaped crystals it has a variable chemical composition but is generally represented by the formula $3Al_2O_3.2SiO_2$. Although mullite occurs naturally, it is usually obtained by heating bauxite with clay or sillimanite. It is presently used as a refractory.

U.S. Pat. No. 4,628,042, issued Dec. 9, 1986 and European Patent Application No. 0130734, published on Jan. 9, 1985, each disclose articles which can be obtained in the form of bodies, which bodies have both the size and shape useful for catalytic and sorptive applications, specifically the oxidation of carbon monoxide or hydrocarbons, as a hydroprocessing catalyst or as a catalyst for asphalt residual processing. It is stated that the mullite articles should have a high surface area, e.g. greater than about 15 $m^2/g$; a high pore volume, e.g. greater than about 0.22 cc/g; and a high concentration of pores of a size in the range of 150 to 350 Angstroms. The desired mullite articles are obtained by calcining kaolin clay and subsequently leaching free silica from the calcined mass to leave porous mullite. It is stated that calcination at or above 1350° C. causes excessive sintering which reduces porosity of the calcined body and extends the required leaching time.

OBJECT OF THE INVENTION

The object of the invention is to provide a porous cellular material which is non-toxic to living cells, has good mechanical rigidity under conditions of high load and when exposed to biochemical treatment fluids, and yet is reversibly permeable to the treatment fluids while retaining cells in its inner cellular structure.

SUMMARY OF THE INVENTION

According to one aspect of the present invention there is provided a porous cellular material comprising a plurality of cavities, each defined by a substantially spherical wall formed of a rigid intermeshing matrix of ceramic needles, said wall being pierced by at least one aperture to provide access to the cavity, the or each aperture having a diameter such that the ratio of the diameter of the aperture to the diameter of the cavity into which the aperture opens is in the range of from 0.1:1 to 1:1.

Each cavity is advantageously defined by the wall of a discrete hollow particle, or microsphere, the wall consisting of intermeshing ceramic needles. Such particles may be formed by a process comprising the following steps:

(a) forming hollow microspheres of an aluminosilicate material having an $SiO_2:Al_2O_3$ molar ratio of at least 0.75:1;

(b) calcining the hollow microspheres formed in step (a) at a temperature in the range of from 1300° C. to 1800° C. for at least one hour;

(c) treating the calcined hollow microspheres with a concentrated aqueous solution of an alkali metal hydroxide at a temperature of at least 50° C. whereby the silica is removed to leave ceramic crystals which define between them interconnecting pores;

(d) washing the alkali metal hydroxide-treated hollow microspheres formed in step (c) until the washing medium is substantially free of silicate and alkali metal ions; and (e) dewatering and drying the washed product obtained in step (d) to obtain microspheres with a wall of the desired porous nature.

Suitable aluminosilicate starting materials include kyanite, sillimanite and andalusite all of which can be represented by the chemical formula $Al_2O_3.6SiO_2$; dumortierite which can be represented by the chemical formula $8Al_2O_3.B_2O_3.6SiO_2.H_2O$; clay minerals of the kandite group which can be represented by the chemical formula $Al_2O_3.2SiO_2.2H_2O$ and pyrophillite which can be represented by the chemical formula $Al_2O_3.4SiO_2.H_2O$. Other possible aluminosilicate starting materials include topaz, pinite, illite and clay minerals of the smectite class. It is also possible to use as the aluminosilicate starting material a mixture of an alumina-rich material and a silica-rich material or a mixture of substantially pure alumina and silica, provided that the molar ratio $SiO_2:Al_2O_3$ is at least 0.75:1 and preferably at least 1:1 in each case. We have found clay minerals of the kandite class, namely kaolinite, dickite, nacrite and halloysite, to be most suitable and, in particular, kaolin clay which consists predominantly of kaolinite. Still further examples of aluminosilicate starting material include magnesium aluminium silicates such as talc. In this case, after the material has been subjected to steps (a) to (e) above, the product will consist of microspheres with a porous shell of cordierite of chemical formula $2MgO.2Al_2O_3.5SiO_2$.

The hollow microspheres are preferably obtained by spray drying an aqueous suspension of the aluminosilicate material, the suspension containing from 20% to 60% by weight of solid aluminosilicate material and from 0% to 40% by weight, based on the weight of dry aluminosilicate material, of a viscosifying agent. Conventionally spray drying is performed by spraying, into a suitable vessel in which hot gases are circulated, an aqueous suspension containing from 60% to about 80% by weight of solids. However, this tends to form particles which are dense and substantially free of an internal cavity. If, however, the solids content of the feed suspension is reduced each droplet formed by atomisation of the feed suspension tends to dry first on the outside leaving a hard impermeable skin enclosing a substantially spherical volume of water. On further exposure to the hot gases in the spray dryer chamber the water turns to steam which blows a hole through the outer skin.

A viscosifying agent is generally necessary to ensure that droplets of the desired size are formed by the atomising means in the spray dryer. The viscosifying agent may be a water dispersible synthetic polymer such as poly(vinyl acetate) or poly (vinyl alcohol), or a water dispersible natural polymer which may be, for example, carbohydrate-based, such as dextran, starch, agar, guar gum, hydroxyethyl cellulose of sodium carboxymethyl cellulose or protein-based, for example casein or gelatin.

Preferably, the particulate product of step (a) has a narrow range of particle sizes. For example, an especially advantageous product comprises particles substantially all of which are between 10 microns and 100 microns in size.

Although each cavity is advantageously defined by the wall of a discrete particle, or microsphere, a porous material in which a plurality of individual cavities are formed in a relatively large unit having a rigid foam-like structure is also within the scope of the present invention. Such a material may be prepared by forming a foam from a suspension containing from 20% to 60% by weight of solid aluminosilicate material, and drying the wet foam to form a substantially rigid cellular body. Still further, microspheres may be fused together to form pellets or bodies of various shapes and sizes, each body comprising a plurality of individual microspheres. Such bodies may be formed by subjecting microspheres, formed by the spray-drying method and under the conditions described above, to light pressing in a mould of appropriate dimensions, for example a tablet press, and calcining the resultant pressed body under the conditions specified above.

The aluminosilicate material prepared as described above by spray drying or by foaming is then heat-treated by the process known as soak calcination in, for example, a tunnel kiln, in which the material is exposed to a temperature in the range of from 1300° C. to 1800° C. for at least 1 hour. Preferably, the material is heat-treated at a temperature greater than 1350° C. but not greater than 1600° C. for a time in the range of from 5 hours to 24 hours. After heat-treatment by soak calcination the mixture of ceramic crystals and silica is comminuted and subjected to one or more particle size separations by sieving, air classification and/or centrifugal or gravitational sedimentation.

If in step (b) the silica in the heat-treated mixture of ceramic crystals and silica is to be readily soluble in the concentrated aqueous solution of an alkali metal hydroxide then the aluminosilicate starting material should preferably contain from 1.5% to 2.5% by weight of $M_2O$ where M is sodium and/or potassium. If the starting material contains less than this amount of $M_2O$, the $M_2O$ content may be increased by adding an appropriate quantity of an $M_2O$-containing mineral, such as feldspar.

In step (c) the alkali metal hydroxide is most conveniently sodium hydroxide and the molarity of the alkali solution is preferably at least 3M. Advantageously, the reaction between the hollow microspheres of step (a) and the alkali metal hydroxide solution is performed at a temperature between 80° C. and the boiling point of the alkali metal hydroxide solution.

The purpose of step (c) is to dissolve substantially completely from the mixture of ceramic material and silica, the silica component which is generally present in a glassy form. After the silica has been removed by dissolution each particle consists predominantly of ceramic needles joined together in the form of a three-dimensional lattice which has a high proportion of interconnecting voidage, the passages of which are relatively wide in relation to the width of the ceramic needles.

After Leaching with the alkali metal hydroxide solutions, the calcined cellular body is washed and dried as described in steps (d) and (e) above.

In step (d) the alkali-treated particulate product of step (c) is preferably washed first with an alkaline solution weaker than that used in step (c) and then repeatedly with water until the washing medium is substantially free of silicate and alkali metal ions. The alkaline solution used in this washing procedure preferably has a molarity of 1M or less.

The dry particulate product obtained on carrying out step (e) is found to have good mechanical properties when packed into a column. In particular the particles are resistant to crushing and abrasion and can withstand a high differential pressure between one end of the column and the other when a liquid is pumped through the column.

The ceramic needles forming the walls of the porous cellular material of the present invention preferably consist of mullite. Since the melting point of mullite is about 1810° C. the particular product can be subjected to high temperatures for long periods without fusing or sintering, and it has been found that the material has good resistance to thermal shock, being able to withstand repeated quenching from 1200° C. to room temperature with no deleterious effect on its structure. The cellular porous material formed from mullite is also able to withstand prolonged exposure to strong acids of pH 1 and strong alkalis of pH 14. Of the known comparable materials silica is soluble in strongly alkaline solutions and alumina and clays are attacked by strong acids.

It is preferred that each cavity of the porous cellular material has an overall diameter in the range of from 5 microns to 5 mm and, most advantageously, an overall diameter in the range of from 20 microns to 120 microns. The wall thickness is preferably in the range of from 2 microns to 20 microns, more preferably from 5 microns to 10 microns.

When the material of the present invention is a particulate mass of microspheres, prepared using the spray drying technique, it is preferred that each microsphere has an overall diameter of from 5 microns to 5 mm, more preferably 20 microns to 120 microns. It is important that all, or substantially all, of the particles are not smaller than 5 micrometers, in order to ensure that a column packed with the material has a good flow velocity, and are not larger than 5 millimeters, and preferably not larger than 1 mm, in order to ensure that a column packed with the material has a good surface area per unit weight. The shell of each microsphere is pierced by one, two or three apertures, most preferably by a single aperture, and the ratio of the diameter of the aperture to the overall diameter of the microsphere is preferably in the range from 0.1:1 to 0.75:1. The volume of the internal cavity of each microsphere is preferably from 50% to 90% of the volume of the microsphere if the microsphere is to capture and retain a useful number of biological cells.

It is preferable that the hollow, substantially spherical microspheres have at least a degree of anisotropy in order that the units may capture, by means of hydrodynamic forces, biological cells from a liquid suspension which is caused to flow past them. Hydrodynamic studies have suggested that when a fluid is flowing over a smooth surface in which is formed a cavity the shape of the entrance to which is regular and symmetrical, one of more eddies are set up within the cavity but substantially no mixing takes place between the eddies and the main fluid flow over the surface. These findings appear to apply over a very wide range of Reynolds numbers for the flow over the surface. If, however, the entrance to the cavity is anisotropic, mixing will occur at all Reynolds numbers between the eddies and the flow over the surface. It is believed that the particles formed by the sequence of spray drying a suspension of particulate material followed by calcination as described above have a desirable degree of anisotropy. Nevertheless, it is believed that, even if the particles of the invention are isotropic they would still be able to capture biological cells. Thus, when the material comprising substantially spherical units in accordance with the invention is packed into a column and a liquid suspension of biological cells is passed through the column, the cells are captured and caused to pass through the apertures into the internal cavities primarily as a result of hydrodynamic forces. The capture and retention of the cells by the substantially spherical units is aided by the fact that the shell of each unit has pores of such size that it is permeable to the suspending liquid but impermeable to the cells.

Preferably, where the outer shell of the microsphere is mullite, the shell comprises an intermeshing matrix of mullite needles having a width generally in the range of from 0.1 microns to about 0.5 microns. The pores defined between the needles preferably are in the range of from 0.1 to 1.0 microns i.e. of a width to permit penetration of nutrients and material essential to the immobilised cell for growth. The crystals of mullite are preferably substantially uniform in size, preferably having a length in the range of from 1 micrometer to 5 micrometers, and the interconnecting pores preferably have a width no greater than 2 micrometers and a width preferably no smaller than 0.1 micrometer, more preferably no smaller than 0.5 micrometer.

The specific surface area of the particulate porous material of the present invention, as determined by the B.E.T. nitrogen adsorption method, is less than 10 $m^2$ per gram, and usually is less than 7 $m^2$ per gram.

When prepared by spray drying, the hollow spheres, before calcination, are usually produced with openings communicating with the internal cavities. Alternatively, the spray dried particles may be produced with a wall which is thinned at certain regions which regions, after calcination, are held together by silica. On leaching, their thinned regions will break to yield openings into the internal cavity. This phenomenon may also occur in the preparation of a porous particulate material by the foaming method.

It is important that the internal cavities of the porous cellular material should have sizes in the range of from 5 microns to 5 mm in order to accommodate the penetration and immobilisation of a variety of prokaryotic and eukaryotic cells whose diameters are in the range from 0.5 to 3 microns, and up to 40 microns, respectively.

The prokaryotic cells may be able to penetrate the particles through the array of ceramic, e.g. mullite, crystals. However, to enable eukaryotic cells to enter the internal cavities within the porous material, it is important that openings are provided in the particle wall in the case of the hollow spherical particles and, in the case of a rigid foam, that openings between internal cavities in the foam and the outside of the particle are provided. Such openings into the internal cavities should be at least 5 micrometers in diameter, but may be up to fifty micrometers in diameter.

A serious problem in biotechnology is the retention of eukaryotes and prokaryotes such as bacteria, moulds and yeasts in reactors. The loss of cellular material has to be minimised as far as possible in order to increase the efficiency of the biotechnological process and thus reduce reactor volume and residence time.

Immobilised cells can be described as cells which are physically confined or localised in a certain defined region of space with retention of their catalytic activities and which can be used repeatedly and continuously (see Chibata, I. (1978) "Immobilised enzymes: Research and Development", John Wiley and Sons, New York; P.7. which is incorporated herein by reference). The study of immobilised cells to produce chemicals has expanded rapidly in the last decade (see (i) Abbott, B. J. (1977) Immobilised cells. "Annual Reports on Fermentation Processes 1", Perlman, D. (ed.), Academic Press, London, pp. 205–233; (ii) Abbott, B. J. (1978) Immobilised cells, "Annual Reports on Fermentation Processes 2", Perlman, D. (ed.), Academic Press, London, pp. 91–123; (iii) Messing, R. A. (1980) Immobilised microbes, "Annual Reports on Fermentation Processes 4", Tsao, G. T. (ed.), Academic Press, London, pp. 105–121; (iv) Chibita, I. and Tosa, T. (1981) Use of immobilised cells. Annu. Rev. Biophys. Bioeng. 10:197-26; (v) Fukui, S. and Tanaka, A. (1982) Immobilised microbiol cells. Annu. Rev. Microbiol. 26:145-172; and (vi) Bucke, C. (1983) Immobilised cells. Phil. Trans. R. Soc. Lond. B 300:369-389. (These reviews are incorporated herein by reference). More recently, interest in the application of immobilised living cells to the synthesis of biologically-active macromolecules, such as antibiotics and enzymes, has increased.

As the utility of cell immobilisation with respect to re-usability becomes proven, efforts have been directed towards better means of immobilisation.

The requirements of a high quality biosupport for cell immobilisation can be outlined as follows:
(i) loss in activity on immobilisation should be low;
(ii) high cell loading should be possible;
(iii) substrate and products should be able to diffuse freely through the biosupport;
(iv) the biosupport should have a good mechanical strength and good resistance to abrasion;
(v) the biosupport should be thermally and chemically stable;
(vi) regeneration of the biosupport should be possible; and
(vii) the biosupport should offer a high contact area.

The porous cellular materials in accordance with this invention are particularly suited to application as biosupports.

Thus, according to another aspect of this invention, there is provided a biological support comprising a porous cellular material comprising a plurality of cavities each defined by a substantially spherical wall formed of a rigid intermeshing matrix of ceramic needles said wall being pierced by at least one aperture to provide access to the cavity, and the or each aperture having a diameter such that the ratio of the diameter of the aperture to the diameter of the cavity into which the aperture opens is in the range of from 0.1:1 to 1:1, at least some of each the cavities having immobilised within the structure thereof a biological component selected from the group consisting of biological macromolecules and biological cells.

If the biological component is an enzyme or a prokaryotic cell, it may be immobilised within the interconnecting pores of the matrix of ceramic, e.g. mullite, crystals. However, if the biological component is an eukaryotic cell, it will be immobilised within an internal cavity of the substantially cellular particles.

BRIEF DESCRIPTION OF THE DRAWINGS

FIG. 21 is a graph showing the rate of growth of cells retained in particles in accordance with the invention and supplied with a nutrient fluid under standard conditions.

EMBODIMENTS OF THE INVENTION

The invention is illustrated by the following Examples.

EXAMPLE 1

(a) A Cornish kaolin clay having a particle size distribution such that 36% by weight consisted of particles having an equivalent spherical diameter smaller than 2 microns and 30% by weight consisted of particles having an equivalent diameter larger than 10 microns, and containing 1.7% by weight of $D_2O$, was fired in a tunnel kiln under conditions such that it was exposed to a temperature of 1500° C. for 8 hours.

Figure 1:
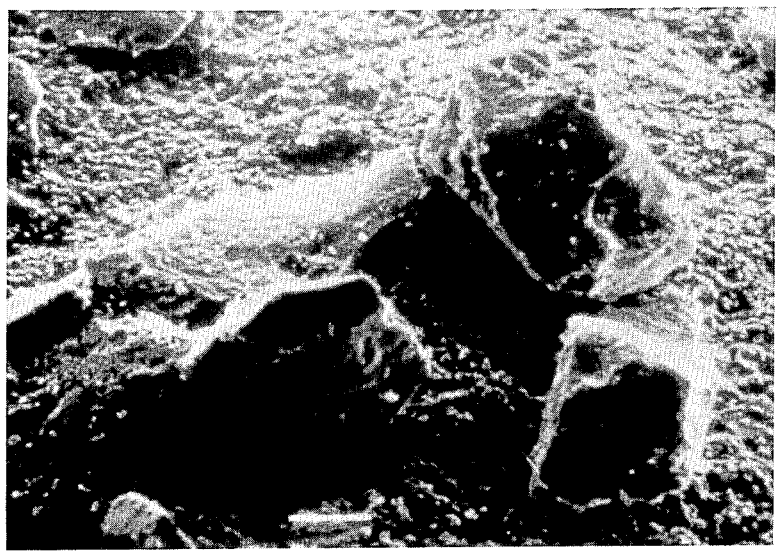
FIG. 1 shows particles comprising mullite crystals set in a glassy phase, as produced in Example (1a)
Figure 2:
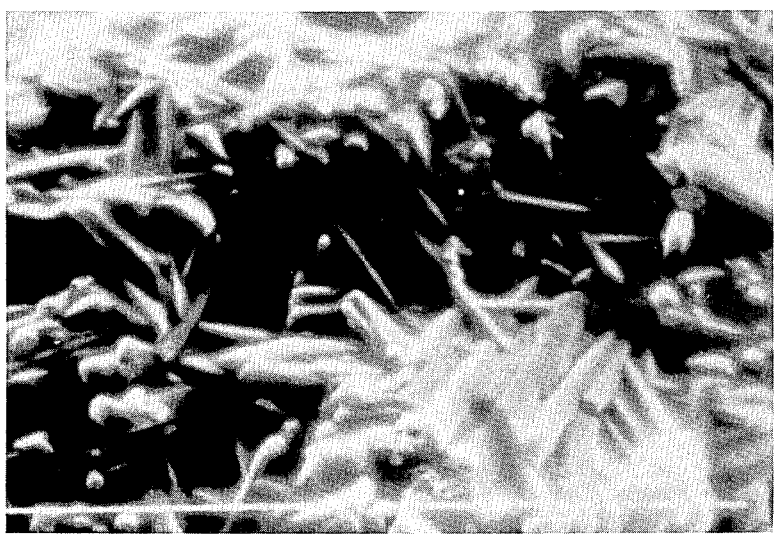
FIG. 2 is an enlarged view of the mullite crystals in the particles shown in FIG. 1.

After cooling, the calcined material, which comprised mullite crystals set in a glassy silica phase (see FIGS. 1 and 2), was crushed and ground and the comminuted material was subjected to particle size separation by sieving. The material passing a No. 200 mesh British Standard sieve (nominal aperture 76 microns) was selected for further processing and was subjected to air classification to remove substantially all particles smaller than 10 microns.

(b) A sample of this particulate material was then boiled with 100 ml of 5M sodium hydroxide for 1 hour. The liquor was then removed using a centrifuge.

(c) The solid material was washed with water, the washings also being removed by centrifuge.

(d) The washed solid material was then dried in an oven at 60° C. and the dry cake milled in a Janke and Kunkel laboratory analytical mill.

Atomic absorption analysis of the liquor and washings showed that the amount of silica removed was 26.4% by weight of the total weight of the heat-treated kaolin (the theoretical proportion of the glassy silica phase in heat-treated kaolin is 38.6% of the total weight).

Figure 3:
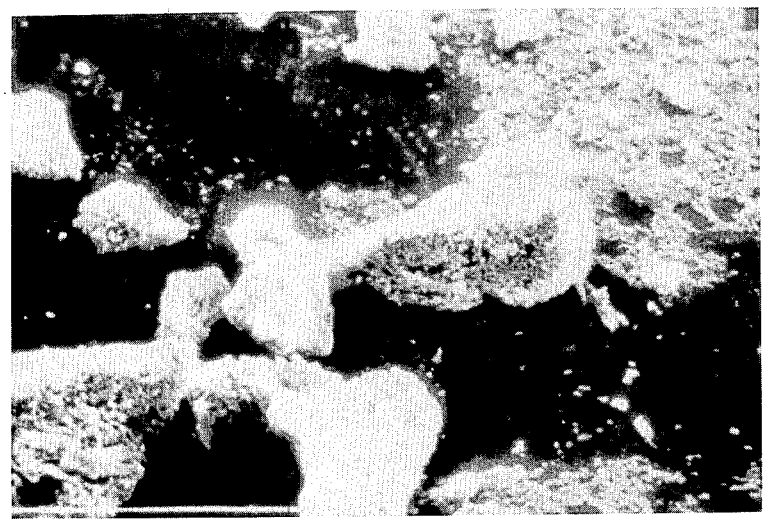
FIG. 3 shows similar particles to those shown in FIG. 1, with the glassy phase removed.
Figure 4:
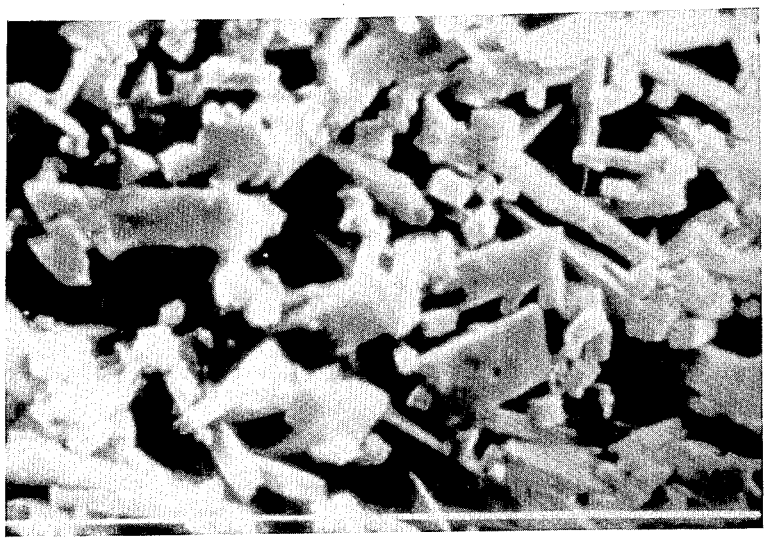
FIG. 4 is a close-up view of the mullite crystals in the particles shown in FIG. 3.

Scanning electron micrographs (see the accompanying FIGS. 3 and 4) show that the particles had a surface consisting of an exposed three dimensional matrix of mullite crystals in which substantially all of the mullite needles have a length in the range from 1 micron to 5 microns and define between them interconnecting pore 5 having a width in the range from about 5 nanometers to about 2 microns.

Figure 5:
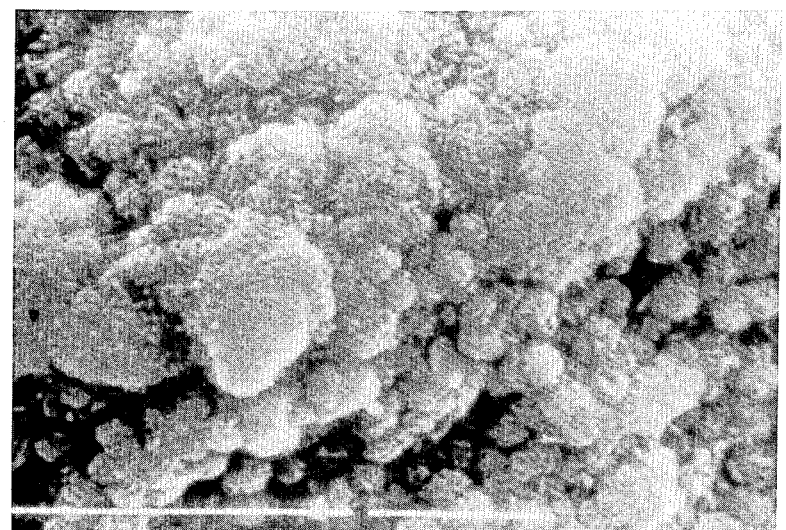
FIG. 5 shows the structure of a product prepared in the same manner as the product shown in FIGS. 3 and 4, except that calcination was conducted at a lower temperature.

By comparison, calcination of the same Cornish kaolin clay in a muffle furnace at 1200° C. for 1 hour, followed by crushing and sieving the cooled product, boiling with sodium hydroxide solution, washing with water, and drying as described under steps (b), (c), and (d) above produced material consisting of mullite needles all of which were smaller than 1 micron in length, typically 0.5 micron in length. The interconnecting pores in this material were typically from 10 nm to 100 nm (0.1 micron to 0.1 micron) in diameter as can be seen from FIG. 5.

EXAMPLE 2

Further 15 g samples of the particulate heat-treated kaolin prepared as described in Example 1 were boiled with 250 ml of 5M sodium hydroxide solution for varying lengths of time. In each case the liquor was separated and the alkali-treated material washed, dried and comminuted as described in Example 1. In each case the liquor and washings were subjected to atomic absorption analysis for silicon and the amount of silica removed, expressed as a percentage of the total weight of the heat-treated kaolin, was calculated in each case. The results obtained are set forth in Table 1 below:

TABLE 1

| Treatment time (hours) | Silica removed (% by weight) |
|---|---|
| ½ | 16.9 |
| 1 | 25.3 |
| 2 | 26.6 |
| 4 | 27.8 |

It can be seen that a significant proportion of the glassy silica phase was removed on boiling for only ½ hour and there is little advantage to be obtained by prolonging the time of boiling beyond 1 hour.

EXAMPLE 3

Further 15 g samples of the particulate heat-treated kaolin prepared as described in Example 1 were boiled for 1 hour with 250 ml of sodium hydroxide solutions of varying molarity. In each case the liquor was separated and the alkali-treated material washed, dried and comminuted as described in Example 1. In each case the liquor and washings were subjected to atomic absorption analysis for silicon and the weight of silica removed, expressed as a percentage of the total weight of the heat-treated kaolin, was calculated in each case. The results obtained are set forth in Table 2 below:

TABLE 2

| Molarity of NaOH Solution | Silica removed (% by weight) |
|---|---|
| 1M | 11.5 |
| 3M | 21.2 |
| 5M | 25.3 |
| 7M | 25.8 |

These results show that the molarity of the sodium hydroxide is preferably at least 3M but that there is little advantage in increasing the molarity above 5M.

EXAMPLE 4

Further 15 g samples of the particulate, heat-treated kaolin prepared as described in Example 1 were contacted for 1 hour with 250 ml of 5M sodium hydroxide solution at varying temperatures. In each case the liquor was separated and the alkali-treated material washed, dried and comminuted as described in Example 1. In each case the liquor and the washings were subjected to atomic absorption, analysis for silicon and the weight of silica removed, expressed as a percentage of the total weight of the heat-treated kaolin, was calculated in each case. The results obtained are set forth in Table 3 below:

TABLE 3

| Treatment temperatures °C. | Silica removed (% by weight) |
|---|---|
| 25 | 0.07 |
| 50 | 1.3 |
| 75 | 4.7 |
| 100 | 25.3 |

These results show that it is important that the particulate heat-treated kaolin is contacted with sodium hydroxide solution at a temperature close to the boiling point of the solution.

EXAMPLE 5

(a) A sample of the same kaolin clay as was used in Example 1 was vigorously mixed with sufficient water to form a suspension containing 65% by weight of dry kaolin and 0.6% by weight, based on the weight of dry kaolin, of tetrasodium pyrophosphate as a dispersing agent. The resultant suspension was then diluted with water to a solids content of 40% by weight and was beaten for 10 minutes in a household food mixer in the presence of 1% by weight, based on the weight of dry kaolin, of the surfactant n-octylamine phosphate. The resultant wet foam was transferred to an open pan and dried for 16 hours at 80° C. in an oven and then heat-treated for 4 hours at 1000° C. to ensure that the foam was well set. The substantially rigid foam was fired in a tunnel kiln under conditions such that it was exposed to a temperature of 1500° C. for 8 hours. After cooling, the calcined material was lightly crushed and the comminuted material was subjected to particle size separation by sieving on a No. 200 mesh British Standard sieve.

(b) 1 g of the particulate material passing through the sieve was boiled with 100 ml of 5M sodium hydroxide for 1 hour. The liquor was removed using a centrifuge.

(c) The sample was washed with water, the washings also being removed by centrifuge.

(d) The washed sample was then dried in an oven at 60° C. and the dry cake milled in a Janke and Kunkel laboratory analytical mill. The product was tested as described in Example 8 below.

EXAMPLE 6

Figure 6:
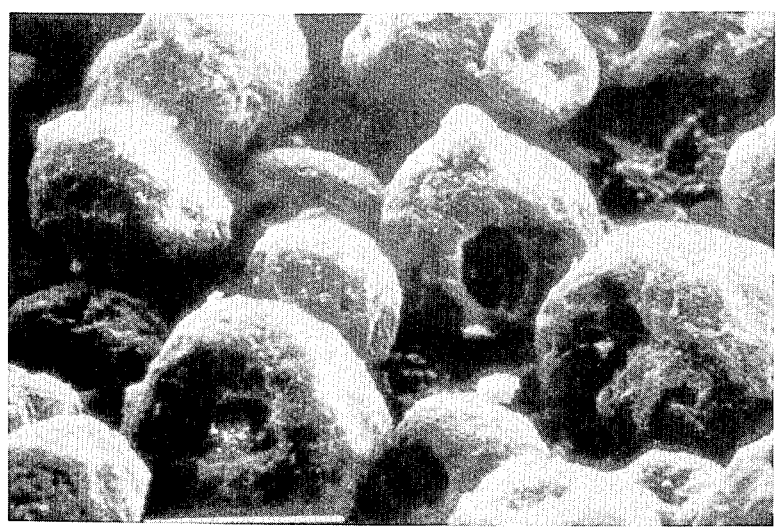
FIGS. 6 and 7 show a particulate product produced by spray during a suspension of kaolin clay.
Figure 7:
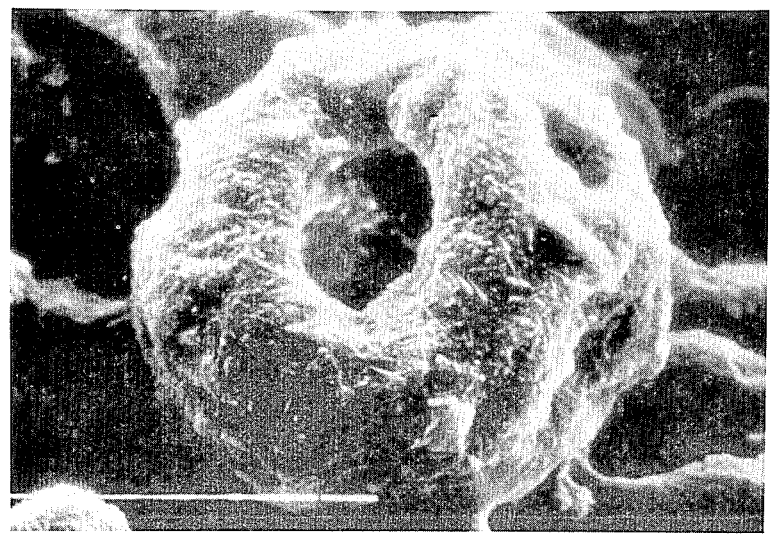

A sample of the same kaolin clay as was used in Example 1 was vigorously mixed with sufficient water to form a suspension containing 62% by weight of dry kaolin and 0.6% by weight, based on the weight of dry kaolin, of tetrasodium pyrophosphate. The resultant suspension was then fed at a rate of approximately 1 liter per minute to a laboratory spray dryer operating at an inlet temperature of 380° C. and an outlet temperature of 175° C. The dried product which was in the form of substantially spherical hollow bodies of substantially uniform diameter of about 50 microns (see FIGS. 6 and 7) was fired in a tunnel kiln under conditions such that it was exposed to a temperature of 1500° C. for 8 hours.

Figure 8:
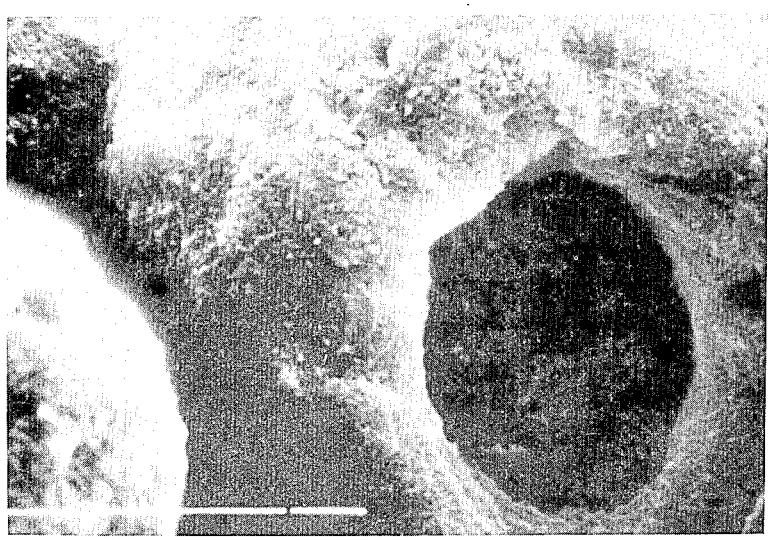
FIGS. 8 and 9 show a particulate product produced by removing the glassy silica phase from the particles shown in FIGS. 6 and 7.
Figure 9:
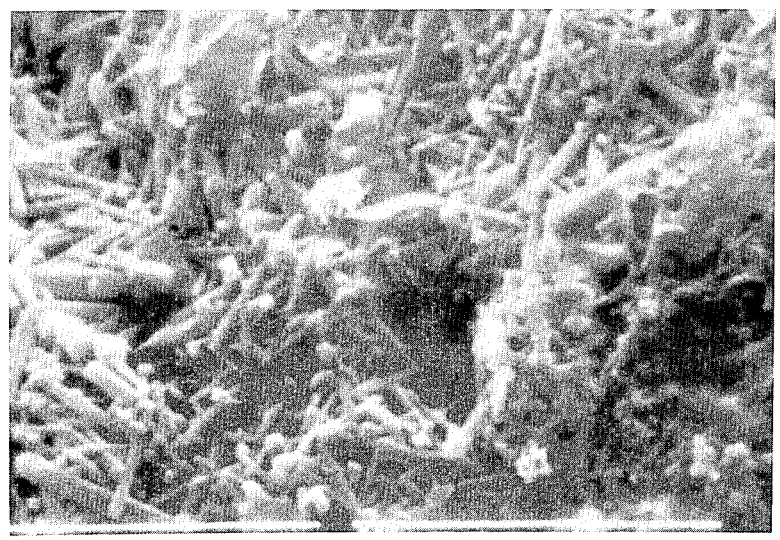

After cooling, the calcined material was lightly crushed to separate the spheres which had become fused together during the firing and the crushed material was dividing into two portions A and B. Portion A was reserved for further testing as described in Example 8 below, while 1 g of Portion B was treated with sodium hydroxide under identical conditions to those described in Example 5 and the treated material was centrifuged, washed, dried and milled in the same way to produce a porous particle containing a large internal cavity as is shown in FIGS. 8 and 9.

Figure 10:
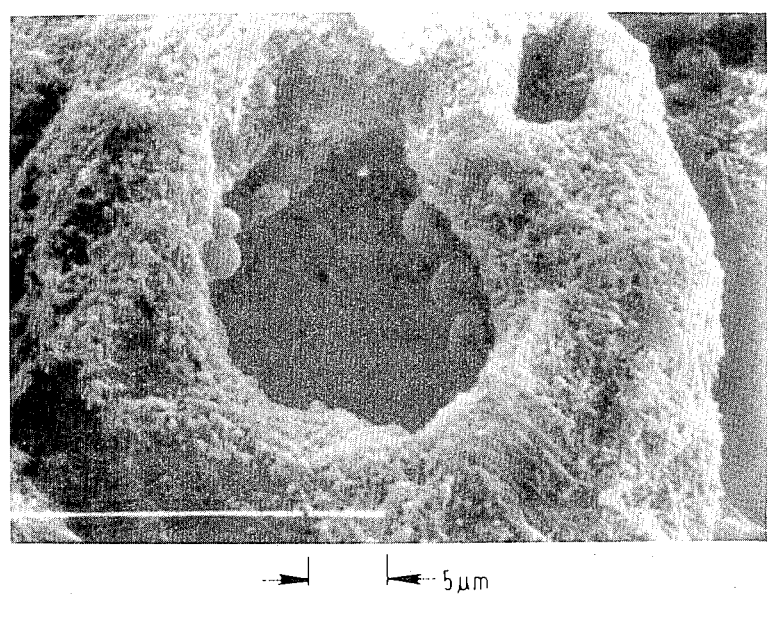
FIGS. 10 and 11 each show a particle similar to those shown in FIGS. 8 and 9, having a number of yeast cells immobilised thereon.
Figure 11:
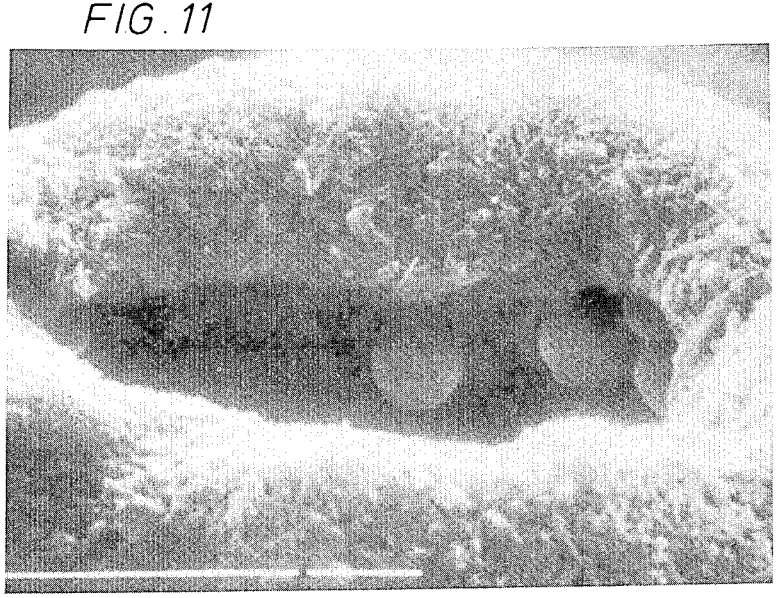

The hollow spheres produced may be used as a biological support on which a biological component may be immobilised. FIGS. 10 and 11 each show a substantially spherical mullite particle of this invention having a large internal cavity in which a number of yeast cells have been immobilized. To produce the structures of FIGS. 10 and 11, a medium containing yeast cells may be passed through a mass of the hollow particles of this invention. On passing through the mass of particles a number of the yeast cells become entrapped and become attached to the inside wall of the hollow particle. In the relatively calm environment of the internal cavity, the yeast cells are not readily disturbed.

EXAMPLE 7

The particulate mullite product of Example 1 was mixed with water to form a suspension containing 10% by weight of dry solids and portions of this suspension were mixed with varying quantities of an aqueous solution, at a temperature of 60° C., containing 10% by weight of the quaternary ammonium compound, di-methyl di-(hydrogenated tallow) ammonium chloride (2M2HT). The mixture was stirred at a temperature of 60° C. for half an hour after which the suspension was filtered and the cake washed with water and dried.

0.5 g of each of the dried products, which consisted of particulate mullite coated with varying amounts of 2M2HT, was mixed with 50 ml of deionised water for 5 minutes in an ultrasonic bath to ensure homogeneity of the suspension. The suspension was then further diluted with deionised water to a solids content of 0.5% by weight and a sample of the very dilute suspension was tested under the microscope in a thin rectangular electrophoretic cell with a potential difference of 80 V between the two electrodes.

The mobility $\mu_E$ of particles in the suspension, or the velocity in cm.s$^{-1}$ under a potential gradient of 1 V.cm$^{-1}$, was determined by measuring the time in seconds taken for a particle to traverse one square of the grid of the microscope. Twenty measurements of the time were made for each sample of suspension, the polarity of the electrodes being reversed after each measurement, and the mean value of the time was used to calculate the value of the velocity $V_E$ of the particles.

The mobility of the particles was calculated from the formula:

$$\mu_E = \frac{V_E}{X}$$

where X is the potential gradient in V.cm$^{-1}$.

The zeta potential, or the difference in potential between the immovable liquid layer attached to the surface of a solid phase and the movable part of the diffuse layer in the body of the liquid, was then calculated from the formula:

$$\rho = \frac{4\pi\eta\mu_E}{\epsilon}$$

where $\eta$ is the viscosity at the operating temperature, and $\epsilon$ is the dielectric constant, of the aqueous medium.

The results obtained are set forth in Table 4 below:

TABLE 4

| Particulate Material | meq. 2M2HT per 100 g of particulate | Mobility (cm·s$^{-1}$) | Surface charge | Zeta potential (mV) |
|---|---|---|---|---|
| Ex. 1 - not NaOH treated | 0 | 4.50 | — | −58.1 |
| Ex. 1 - NaOH treated | 0 | 3.43 | — | −44.3 |
| - NaOH treated | 1 | 3.24 | — | −41.9 |
| - NaOH treated | 3 | 3.03 | — | −39.1 |
| - NaOH treated | 5 | 2.42 | — | −31.9 |
| - NaOH treated | 8 | 5.03 | + | +64.9 |
| - NaOH treated | 10 | 5.01 | + | +64.6 |

These results show that the negative charge on the surface of the particulate material is neutralised when the quantity of 2M2HT absorbed on the surface has a value between 5 and 8 milliequivalents of 2M2HT per 100 g of the particulate material. The surface of the particulate material was found to have a significantly hydrophobic nature when the quantity of 2M2HT adsorbed was 5 milliequivalents per 100 g of particulate material.

EXAMPLE 8

The degree of adsorption of protein to the surface of various particulate materials in accordance with the invention was investigated by adding 1 g of particulate material to 15 ml of an aqueous solution containing 100 ppm of myoglobin and subjecting the mixture to mild agitation in the form of a gentle tumbling action for 18 hours to allow equilibrium to be reached. The mixture was then allowed to stand for 5 hours and centrifuged for 5 minutes at 3000 rpm to separate the particulate material from the solution of unadsorbed protein. The protein content of the initial solution and of the solution of unadsorbed protein separated by the centrifuge were determined by ultra violet spectrophotometry and the difference between the two measurements gave a measure of the quantity of myoglobin in milligrams which was adsorbed by 1 g of particulate material. In most cases the specific surface area of the particulate material was also determined by the B.E.T nitrogen adsorption method. The results obtained are set forth in Table 5 below.

TABLE 5

| Particulate material | Specific Surface area ($m^2g^{-1}$) | myoglobin adsorbed ($mg \cdot g^{-1}$) |
|---|---|---|
| Ex. 1. - not NaOH treated | 0.3 | 0.26 |
| Ex. 1 - NaOH treated | 0.8 | 0.57 |
| Ex. 7. - 5 meq. 2M2HT per 100 g | — | 0.9 |
| Ex. 5. - foamed | 5.1 | 1.2 |
| Ex. 6. Portion A - spray dried, not NaOH treated | 0.9 | 0.2 |
| Ex. 6. Portion B - spray dried, NaOH treated | 1.5 | 0.7 |
| Ex. 6. Portion B coated with 5 meq. 2M2HT per 100 g | — | 0.95 |

These results show that both the specific surface area and the capacity to adsorb protein are increased when the aluminosilicate material consisting predominantly of mullite crystals and silica is treated with concentrated sodium hydroxide solution to dissolve at least part of the silica. A further increase is observed when the aluminosilicate material is prepared from a foamed or spray dried starting material. A still further increase in the capacity to adsorb protein may be achieved by adsorbing about 5 meq. of 2M2HT on the surface of the alkali treated aluminosilicate material thus rendering the surface hydrophobic.

EXAMPLE 9

A kaolin clay having a particle size distribution such that 80% by weight consisted of particles having an equivalent spherical diameter smaller that 2 microns and 0.1% by weight of particles having an equivalent spherical diameter larger than 10 microns was mixed with water to form a suspension containing 40% by weight to dry kaolin, there being mixed with the suspension as a viscosifier 9% by weight, based on the weight of dry kaolin, of sodium carboxymethylcellulose.

Figure 12:
FIG. 12 shows a particle in accordance with the invention.
Figure 14:
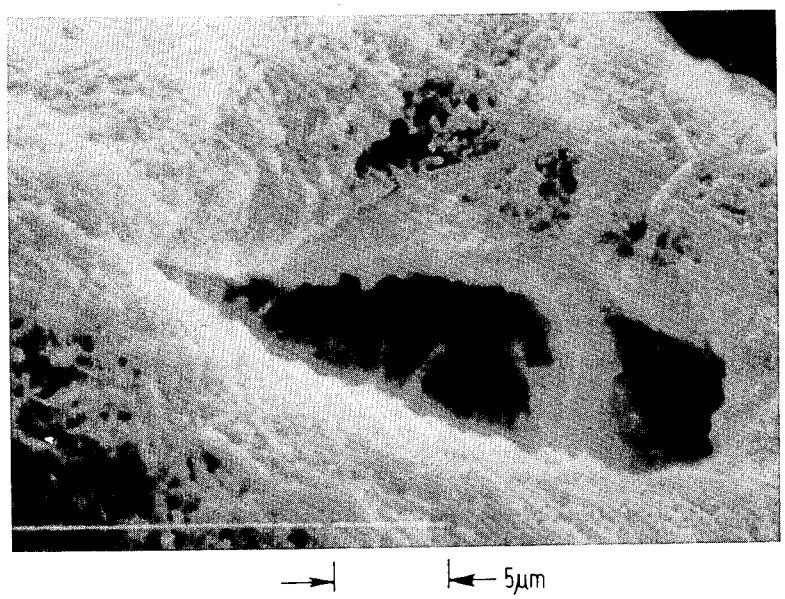
FIG. 14 shows rod-like cells of the bacterium clostridium immobilised in a particle of the type shown in FIG. 12.
Figure 15:
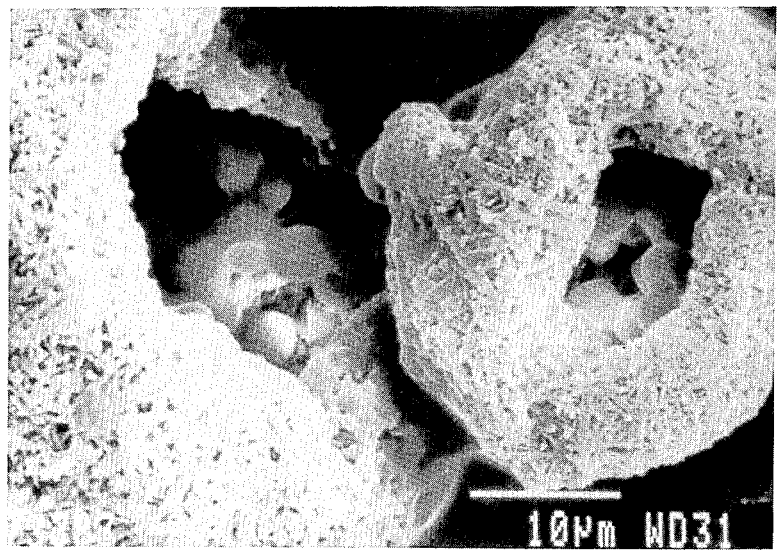
FIGS. 15 and 16 show brewers' yeast cells immobilised in particles in accordance with the invention.
Figure 16:
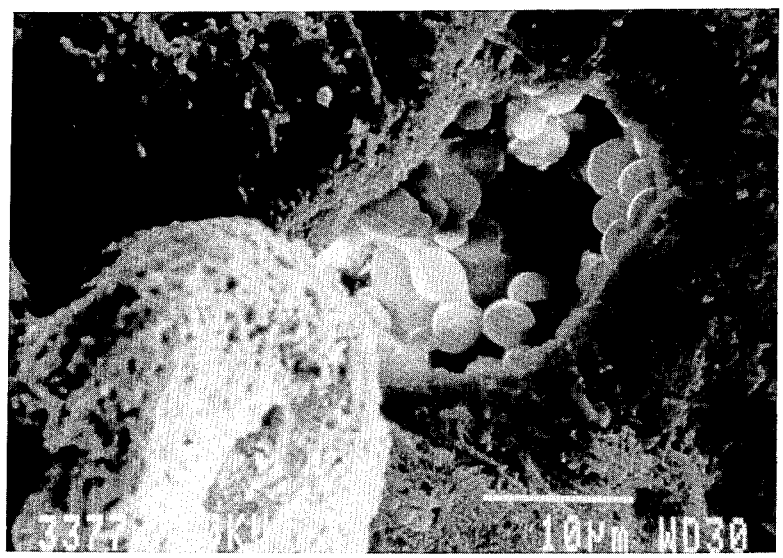
Figure 17:
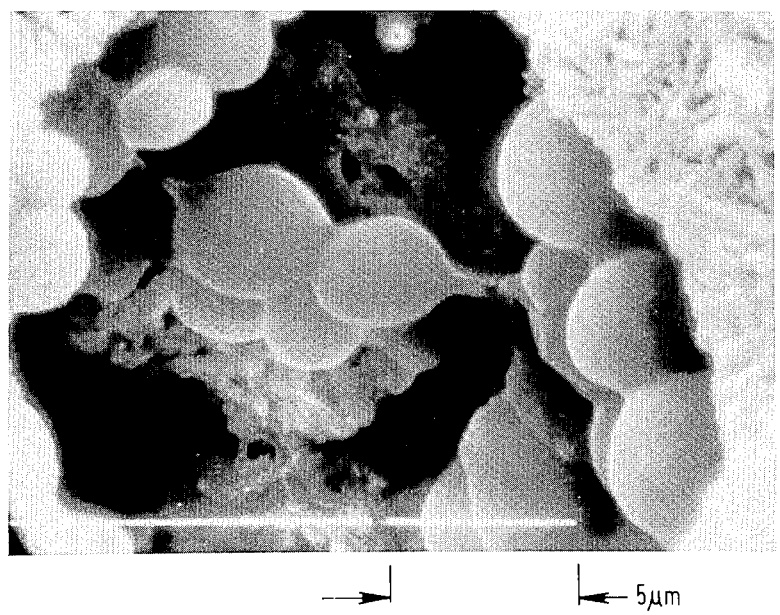
FIG. 17 shows an enlarged view of brewers' yeast cells in the internal cavity of a particle in accordance with the invention.
Figure 17:
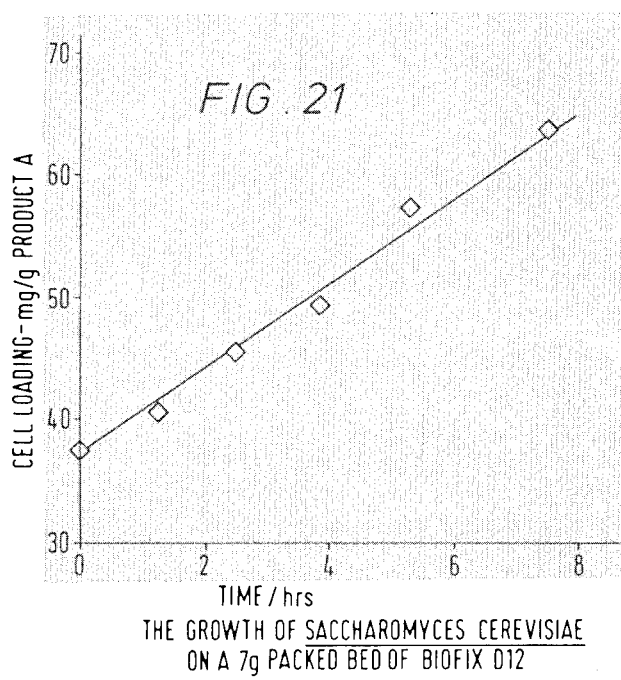
Figure 18:
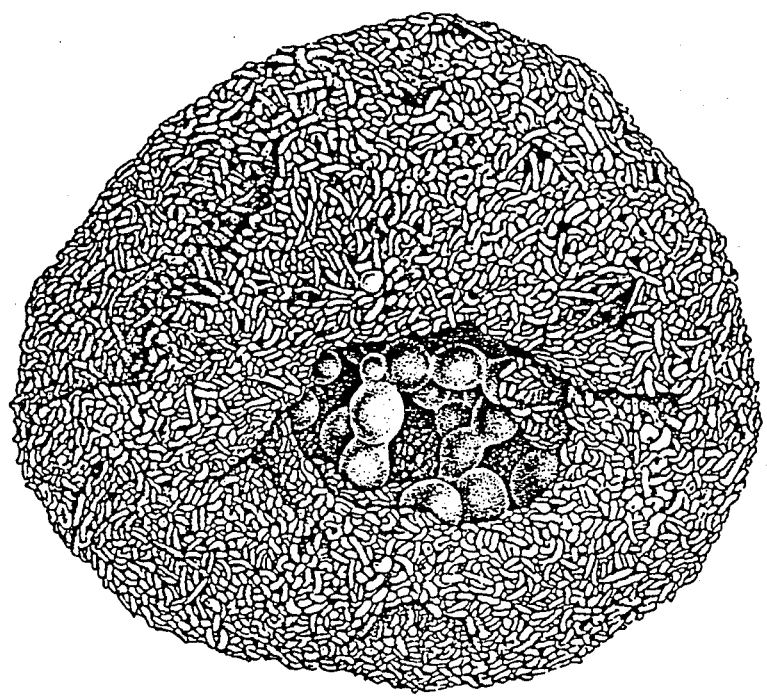
FIG. 18 is an ink drawing of a particle in accordance with the invention showing brewers' yeast cells immobilised in the internal cavity.

This mixture was sprayed by means of a an atomiser at a rate of 380° C. and an outlet temperature of 175° C. The dried product which was in the form of hollow spheres of substantially uniform overall diameter of about 50 microns was calcined in a tunnel kiln under conditions such that it was exposed to a temperature of 1500° C. for 8 hours. The calcined product was then boiled with 3M sodium hydroxide solution for 1 hour to dissolve the silica phase leaving a rigid intermeshing matrix of mullite needles. The liquor was removed by filtration and the particulate product was washed with hot water, the washings also being removed by filtration until the washings were found to be substantially free of sodium and silicate ions. The washed material was then dried in an oven at 60° C. and the dry cake lightly milled to break up any agglomerates. The product was found to consist of hollow particles of overall diameter about 50 microns each having at least one aperture of diameter in the range form 10 to 15 microns. The pores between the mullite needles constituting the shell of the particles were approximately 0.5 microns in width and the volume of the internal cavity was approximately 65% of the overall volume. A particle of this product is shown in FIG. 12 (also see FIG. 14) and has an overall diameter of approximately 50 microns and an aperture diameter of about 1 to 15 microns. Three cells of *saccharomyces cerevisias* (brewer's yeast) can be seen in the internal cavity. This product is referred to as "Product A".

Figure 13:
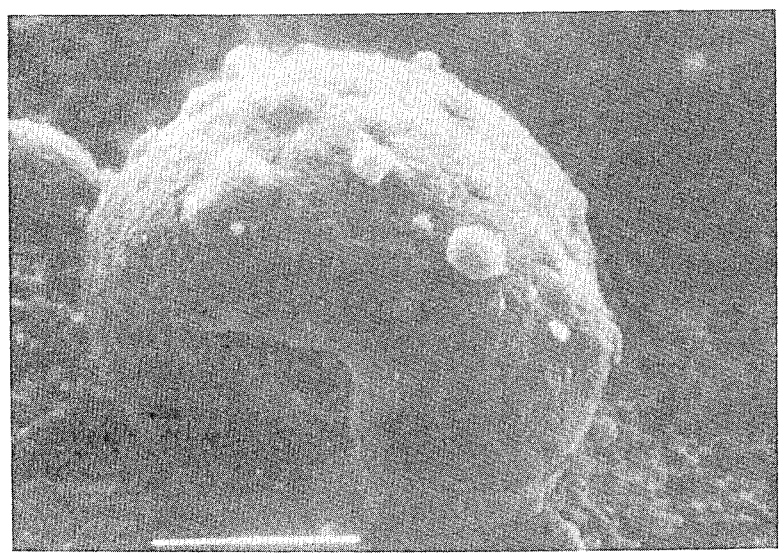
FIG. 13 shows another particle in accordance with the present invention.

A second particulate product in accordance with the invention was prepared using the same starting kaolin and an identical method except that the spray drying conditions were altered to provide a product which was in the form of hollow spheres of substantially uniform overall diameter of about 75-80 microns. The mixture was sprayed into the chamber of the spray dryer by means of an atomiser of different design at a rate of 27-36 liters per minute. The inlet temperature was 400° C. and the outlet temperature 115° C. The final product consisted of hollow particles of overall diameter 75-80 microns each having at least one aperture of diameter in the range form 20-30 microns. The pores between the mullite needles constituting the shell of the particles were approximately 0.5 microns in width and the volume of the internal cavity was approximately 70% of the overall volume. A particle of this product is shown in FIG. 13 and has an overall diameter of about 75 to 80 microns and an aperture diameter of about 20 to 30 microns. The "warts" on the surface of the particle are fine particles which have adhered to the outer surface of the hollow particle during processing. This product is referred to as "Product B".

EXAMPLE 10

Figure 19:
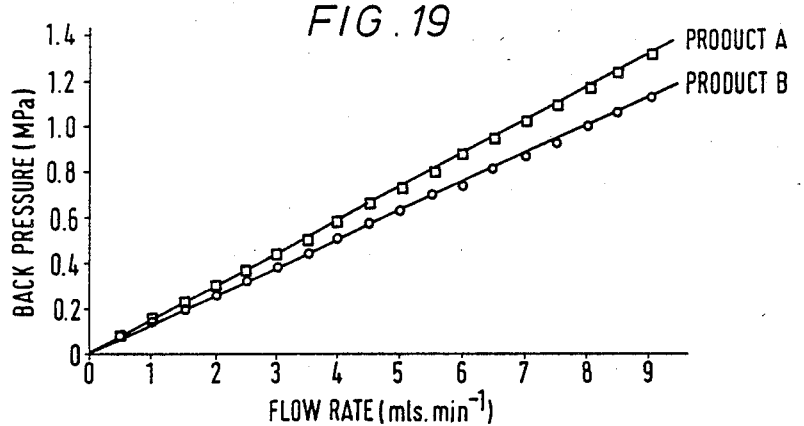
FIG. 19 is a graph showing the relationship between back pressure and flow rate for a liquid medium flowing through a column packed with particles in accordance with the present invention.

The mechanical strength of Products A and B was tested by packing a high performance liquid chromatography column of diameter 7 mm and length 250 mm and fitted at its lower end with a fitted stainless steel disc of pore width 2 microns with each product under a pressure of 8000 psig (55 MPa). In each case a reservoir containing a slurry of the product was connected by means of a pressure coupling to the column and the slurry was forced into the column under pneumatic pressure. A buffer solution comprising 0.25M $Na_2HPO_4$, 0.25M $NaH_2PO_4$, 0.1M NaCl and sufficient NaOH solution to adjust the pH to 6.8 was passed through each column at a series of different flow rates and the back pressure caused by the packing at each flow rate was measured. The results are shown graphically in FIG. 19. The fact that for each particulate product the back pressure increased only linearly with flow rate indicates that there has been no significant breaking down of the particles under a crushing pressure of 55 Mpa to yield fine particles having diameters smaller than about 20 microns which would be detected by blocking the pores of the fritted stainless steel disc.

EXAMPLE 11

A high performance liquid chromatography column identical to that described in Example 2 was packed with Product A under the same conditions as in Example 10 and the resistance of the particulate product to chemical attack by phosphate ions was tested by passing a buffer solution identical to that used in Example 10 through the column at a steady flow rate of 9 ml. $min^{-1}$ for 25 hours. The back pressure caused by the packing was measured at hourly intervals and was found to remain constant at about 185 psi (1.28 MPa) again indicating that there was no breakdown of the particulate material to form fine particles which would block the pores of the sintered stainless steel disc.

EXAMPLE 12

A standard 20 ml syringe of internal diameter 20 mm was packed with 3.5 g of Product A and different volumes of suspension of brewer's yeast cells in a buffer solution were forced through the packed bed in aliquots of 10 ml by means of the syringe plunger at an approximate linear speed of 10 mm.s$^{-1}$. The suspension consisted of 30 g/liter of yeast in 0.2M potassium phosphate solution at pH 7.0. After each volume of the suspension had been forced through the bed, the column was washed with 100 ml of 0.2M potassium phosphate solution and the bed was ejected from the syringe and samples taken from the top and bottom of the bed were assayed for protein content by the Folin method as described by O. H. Lowry, N. J. Rosebrough, A. L. Farr and R. J. Randall in J. Biol. Chem., Vol 193 (1951), page 265. From the results obtained for the protein content the weight of wet yeast cells entrapped in the cavities of the particulate product was calculated using the relationship:

0.14 mg protein=0.28 mg dry yeast cells=1 mg wet yeast cells.

Figure 20:
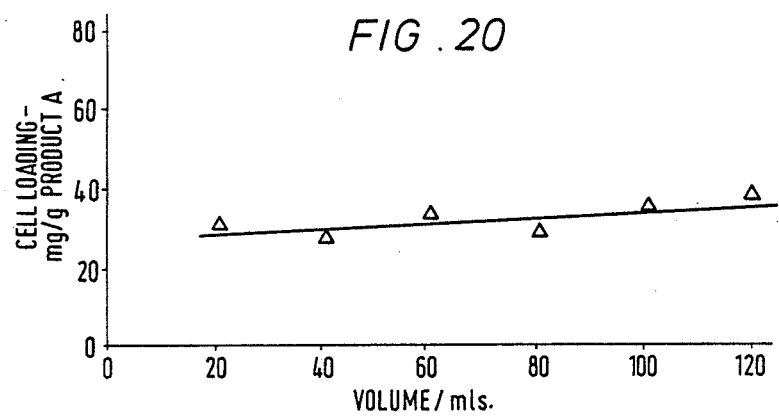
FIG. 20 is a graph showing the relationship between the mass of the cells retained per unit mass of particulate packing material and the mass of cells passed through the packing material in accordance with the invention.

The weight of wet yeast cells entrapped per gram particulate product was plotted against the volume of suspension passed though the packed bed and the resultant graph is shown in FIG. 20.

It will be seen from FIG. 20 that the greatest loading of yeast cells obtained was about 35 mg per gram of particulate product.

The bulk density of Product A is 0.55 g.ml$^{-1}$ and the loading capacity per unit volume was therefore about 19.3 grams of wet cells per liter of wet particulate product.

The experiment was repeated with a particulate product prepared in a manner similar to that of Product A, except that the final leaching with alkali metal hydroxide and washing steps were omitted. The greatest loading of yeast cells achieved for this unleached product was about 15-16 mg per gram of particulate product. This demonstrates that, although yeast cells will enter the cavities of the unleached product by hydrodynamic forces, the rate of entry is enhanced when the particulate product has a porous wall, which permits the suspending medium to wash through the solid support.

The experiment was also repeated using as the packing material a commercial diatomaceous earth biological catalyst support material The greatest loading of yeast cells for this material was about 52 mg of yeast per g. of catalyst support but as the bulk density of this material was only 0.35 g.ml$^{-1}$ the loading capacity per unit volume was about 18.2 g of wet cells per liter of wet catalyst support. It was also found that there was considerable variation between the protein content of the samples taken from the top and bottom respectively of the beds of commercial catalyst support, whereas with the particulate product in accordance with the invention there was no significant variation between the samples taken from the top and bottom of the bed until at least 100 ml of yeast cell suspension had been passed through the bed. The reason that the yeast cells are concentrated at the top of the commercial catalyst support is that the yeast cells tend to be collected by a filtration effect rather than by hydrodynamic effects.

EXAMPLE 13

A standard 20 ml syringe of internal diameter 20 mm was packed with 7 g of Product A and 200 ml of the same suspension of brewers' yeast cells as was used in Example 12 was passed through the packed bed in aliquots of 10 ml by means of the plunger of the syringe. The bed was then flushed with 200 ml of 0.2M potassium phosphate buffer solution to remove any yeast cells which had not been captured and retained by the particulate product. The immobilised yeast cells were then cultured by passing through the bed every hour 10 ml of suspension containing 0.1% by weight of yeast extract and 1% by weight of glucose in 0.2M potassium phosphate solution. At intervals the bed was washed with 30 ml of 0.2M potassium phosphate solution and a sample removed from the bed assayed for protein by the Folin method. From the results of these assays the weight of cells retained per unit weight of particulate product was calculated using the relationship given in Example 12. The results are shown graphically in FIG. 21.

These results show that nutrient solutions can diffuse readily to substantially all of the immobilised cells resulting in rapid and extensive growth of the cells.

We claim:

1. A porous cellular material comprising a plurality of cavities each defined by a substantially spherical wall formed of a rigid intermeshing matrix of ceramic needles selected from mullite or cordierite said wall being pierced by at least one aperture to access to the cavity, and the or each aperture having a diameter such that the ratio of the diameter of the aperture to the diameter of the cavity into which the aperture opens is in the range of from 0.1:1 to 1:1.

2. A porous material according to claim 1, wherein the wall surrounding each cavity consists of intermeshing needles of mullite.

3. A porous material according to claim 1, wherein each cavity is defined by the shell or wall of a discrete particle.

4. A porous material according to claim 1, wherein each cavity has a diameter in the range of from 5 microns to 5 mm.

5. A porous material according to claim 4, wherein each cavity has a diameter in the range of from 20 microns to 120 microns.

6. A porous material according to claim 1, wherein the wall defining the cavities has a thickness in the range of from 2 to 20 microns.

7. A porous material according to claim 6, wherein the wall defining each cavity has a thickness in the range of from 5 microns to 10 microns.

8. A porous material according to claim 1, wherein the wall surrounding each cavity is pierced by a single aperture.

9. A porous material according to claim 1, wherein the ratio of the diameter of the or each aperture to the diameter of the cavity into which the aperture opens is in the range of from 0.1:1 to 0.75:1.

10. A porous material according to claim 3, wherein the volume of each internal cavity of a particle is from 50% to 90% of the volume of the particle.

11. A porous material according to claim 1 wherein a plurality of said cavities are formed in a single body, which body has a structure which is a rigid intermeshing matrix of ceramic needles selected from mullite or cordierite.

12. A porous cellular material according to claim 3, wherein substantially all of the particles of the material are anisotropic.

* * * * *